United States Patent [19]

Cassaday et al.

[11] 4,422,773
[45] Dec. 27, 1983

[54] APPARATUS AND METHOD FOR THE NON-INVASIVE MIXING OF A FLOWING FLUID STREAM

[75] Inventors: Michael M. Cassaday, Peekskill; John L. Smith, New City, both of N.Y.

[73] Assignee: Technicon Instruments Corporation, Tarrytown, N.Y.

[21] Appl. No.: 175,222

[22] Filed: Aug. 4, 1980

[51] Int. Cl.³ .............................................. B01F 5/00
[52] U.S. Cl. .................................... 366/341; 366/348
[58] Field of Search ................... 366/3, 5, 10, 14, 40, 366/101, 106, 126, 336, 337, 338, 339, 340, 341, 348; 138/42, 177, 178, DIG. 11; D23/1; 165/163, 177; 285/169

[56] References Cited

U.S. PATENT DOCUMENTS

| | | | |
|---|---|---|---|
| 2,450,195 | 9/1948 | Grantham | 285/169 X |
| 3,643,925 | 2/1972 | Eubel | 366/126 |
| 3,927,868 | 12/1965 | Moore | 366/341 X |
| 4,222,671 | 9/1980 | Gilmore | 366/337 |

FOREIGN PATENT DOCUMENTS 2032610  5/1980  United Kingdom .

*Primary Examiner*—John W. Shepperd
*Assistant Examiner*—Joseph M. Pitko
*Attorney, Agent, or Firm*—S. P. Tedesco; C. J. Herron

[57] ABSTRACT

New and improved apparatus and method for thorough, non-invasive mixing of a flowing fluid stream, either continuous or segmented, are provided and, as disclosed, are embodied in a mixing conduit which comprises a plurality of interconnected bends, which may be in the form of arcuate coils or sections, successive arcuate sections being operable to establish secondary flow patterns in differing orientations within the flowing fluid stream, or individual segments thereof. Such arcuate sections may be disposed in a same plane, if formed in serpentine fashion, or in non-parallel, preferably orthogonal planes, if formed in a tortuous fashion. Also, the arcuate sections, or a series thereof may be formed in stacked fashion and located in essentially parallel planes.

18 Claims, 12 Drawing Figures

APPARATUS AND METHOD FOR THE NON-INVASIVE MIXING OF A FLOWING FLUID STREAM

BACKGROUND OF THE INVENTION

1. Field of the Invention

This invention relates generally to new and improved apparatus and method for the thorough, non-invasive mixing of a flowing fluid stream and, more particularly, to such apparatus and method as are particularly adapted for use in automated analytical devices of the continuous-flow type.

2. Description of the Prior Art

A variety of non-invasive mixing apparatus and methods are known in the prior art. However, none of the same are operative to effect complete mixing of a flowing fluid stream in presently contemplated high-speed automated continuous-flow analytical systems, for example, as disclosed in pending application for U.S. Letters Pat. Ser. No. 57,541 filed July 11, 1979 and assigned to the assignee hereof. Such systems may require that thorough mixing, at reasonable flow rates and in conduits of reasonable inner diameter, of a blood serum sample and one or more appropriate reagents be effected within less than ten seconds following mixing of sample and reagent. Moreover, since the blood serum samples are passed as a continuous stream comprising successive sample segments separated by inert fluid segments, mixing of the reagent with such successive segments must be effected without adverse effect on the integrity and/or isolation of the successive sample segments, as would result from an invasive mixing device, such as a mechanical stirrer.

For example, a helical mixing coil, as disclosed in U.S. Pat. No. 2,933,293 issued Apr. 19, 1960 to Andres Ferrari and assigned to the assignee hereof, is representative of prior art structures used for mixing in continuous-flow analytical systems. Such mixing coil which is described as relying for mixing primarily upon differences in specific gravities of the liquids to be mixed and which, in any event, markedly limits the mixing effects of secondary flow due to the generally invariant direction of fluid flow in the respective coils of the helix, i.e., counterclockwise as seen in the patent FIG. 8 and the resulting constancy and generally invariant orientation of the secondary flow patterns relative to the coil conduit. Experimental efforts have been made to adapt such helical mixing coils to meet these more stringent mixing requirements, including decreasing the inner diameter of the helix tubing and/or increasing the pitch or tightness of helical winding, with unacceptable results. The increase in back pressure exerted by the flowing fluid stream as a result of such efforts results in unsatisfactory system operation.

OBJECTS OF THE INVENTION

It is, accordingly, an object of our invention to provide new and improved apparatus and method for the rapid and thorough, non-invasive mixing of a flowing fluid stream.

Another object of our invention is the provision of apparatus and method as above which are particularly adapted for use in automated continuous-flow analytical devices.

A further object of our invention is the provision of apparatus as above which are of particularly simple design and construction, and which require the use of only readily available low cost materials of proven dependability in the fabrication thereof, which insures long periods of satisfactory, maintenance-free apparatus operation.

A further object of this invention is to provide apparatus and method to effect complete mixing of a flowing stream along a minimum conduit length.

A further object of this invention is to provide apparatus and method to optimize mixing in a continuous-flow analytical system, while utilizing acceptable flow velocities and inner diameters of the conduits.

A still further object of this invention is to provide apparatus and method for the thorough mixing of each segment of a segmented flowing stream, while precluding contamination between said segments.

SUMMARY OF THE DISCLOSURE

New and improved apparatus and method for thorough, non-invasive mixing of a flowing fluid stream, either continuous or segmented, are provided and, as disclosed, are embodied in a mixing conduit which comprises a plurality of interconnected bends, which may be in the form of arcuate coils or sections, successive arcuate sections being operable to establish secondary flow patterns in differing orientations within the flowing fluid stream, or individual segments thereof. Such arcuate sections may be disposed in a same plane, if formed in serpentine fashion, or in non-parallel, preferably orthogonal planes, if formed in a tortuous fashion. Also, the arcuate sections, or a series thereof may be formed in stacked fashion and located in essentially parallel planes.

"Secondary flow", as described herein, is the result of fluid transiting an arcuate section and is evidenced by a pair of counter-rotating, generally circular flow patterns oriented perpendicular to bulk stream flow and generally symmetrically to a plane of symmetry which coincides generally with the plane of curvature of the arcuate section.

At each successive arcuate section, the secondary flow pattern established by a previous arcuate section is destroyed and a new secondary flow pattern is created in an orientation dictated by the plane of curvature and the direction of circulation of the new arcuate section. In the case of uniplanar structures, the planes of curvature of successive arcuate sections are identical but the direction of circulation of the secondary flow patterns is reversed. While some mixing is achieved by the secondary flow patterns, per se, the destruction and re-establishment of these secondary flow patterns at each successive arcuate section results in very turbulent mixing of a flowing stream having what would otherwise be stable secondary flow patterns. For a given flow velocity, complete mixing is achieved along a substantially reduced conduit length, as compared to prior art structures.

BRIEF DESCRIPTION OF THE DRAWINGS

The above and other significant objects and advantages of our invention are believed made clear by the following detailed description thereof taken in conjunction with the accompanying drawings wherein.

DETAILED DESCRIPTION OF THE INVENTION

Figure 1:
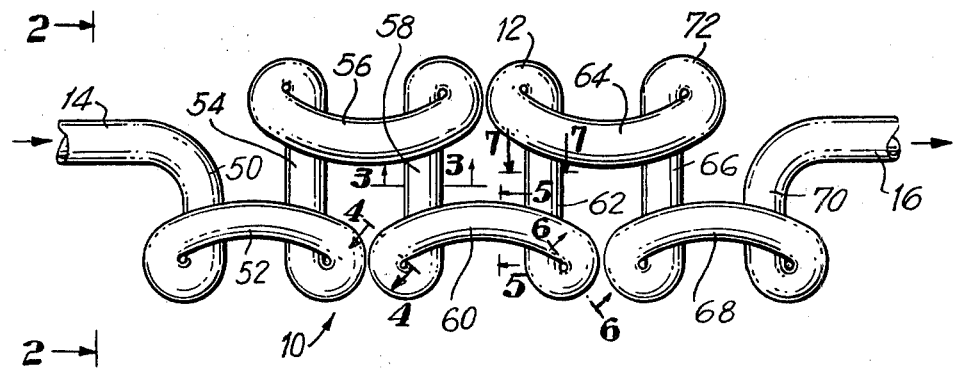
FIG. 1 is a side elevational view of new and improved mixing apparatus constructed and operative in accordance with the teachings of our invention.
Figure 2:
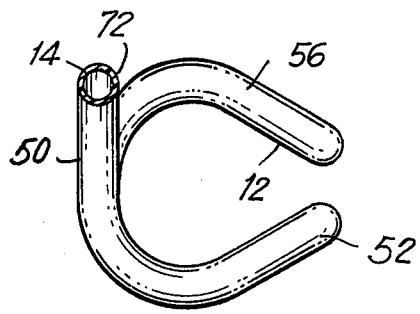
FIG. 2 is a cross-sectional view taken generally along line 2—2 in FIG. 1.

Referring now to FIGS. 1 and 2 of the drawings, the present invention is indicated generally at 10 and basically comprises a mixing coil 12. In operation as briefly described for introductory purposes, a segmented fluid stream, wherein selected segments contain two or more components to be rapidly and thoroughly mixed would be introduced to the mixing coil 12 at the inlet end thereof as indicated at 14 for flow through the coil, and exit of the fluid stream from the outlet end of the coil as indicated at 16. The marked increase, as discussed in greater detail hereinbelow, of the mixing efficiency achieved by the mixing coil 12 as compared, for example, to that provided by the prior art mixing coil of U.S. Letters Pat. No. 2,933,293, as discussed hereinabove, results from an appreciation that the most significant mechanism of mixing in mixing coils of small winding diameter is secondary flow, e.g., flow within the fluid stream which results under laminar flow conditions as here (i.e., relatively low Reynold's numbers certainly well under 2000) from wall friction and centrifugal forces generated by the fluid stream transiting a curve, and which gives rise to two stable, generally symmetrical secondary flow circulation patterns within the fluid stream, all as discussed in greater detail hereinbelow. Repeatedly altering the orientation of the plane of curvature of the relative arcuate coil section, and, accordingly, of the "plane of symmetry" of the secondary flow circulation patterns relative to said coil section, as hereinafter defined and described in detail, results in the repeated destruction and re-establishment of the secondary flow circulation patterns in different orientations relative to said coil section and, hence, increases the overall mixing efficiency.

Figure 8:
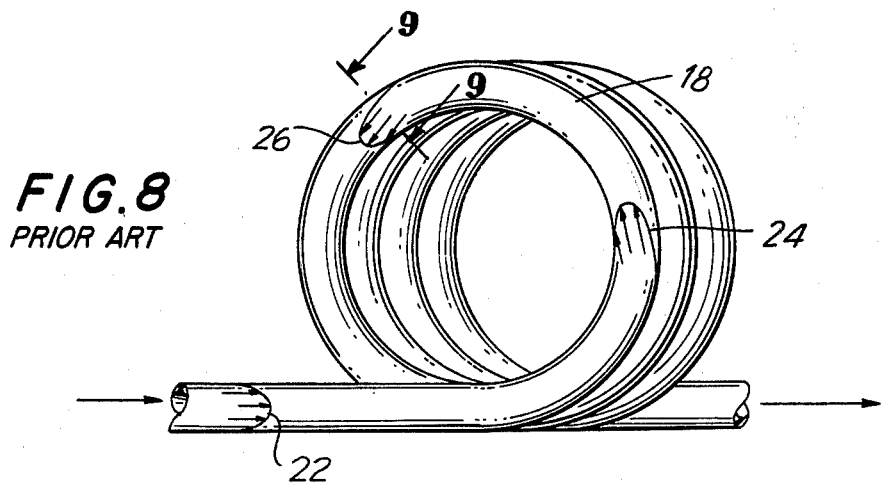
FIG. 8 is a side elevational view of a representative, prior art helical mixing coil.
Figure 9:
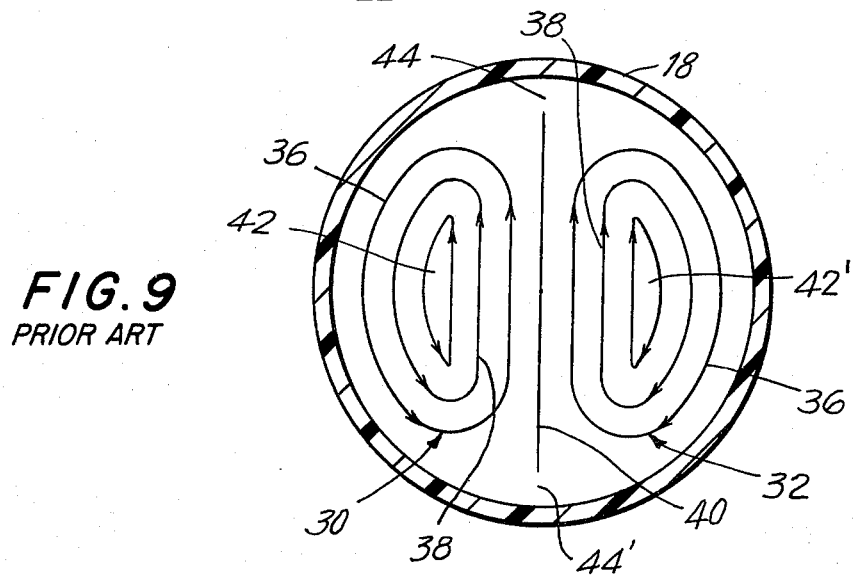
FIG. 9 is a somewhat enlarged cross-sectional view taken generally along line 9—9 in FIG. 8.

More specifically, FIGS. 8 and 9 illustrate the phenomenon of secondary flow in a fluid stream flowing in a representative prior art helical mixing coil and, also, illustrate the significant limitations of the mixing effects of secondary flow which are inherent in such mixing coil. As a fluid stream flows in the indicated direction through a representative initial coil 18 of a prior art helical mixing coil, stable secondary flow circulation patterns will be developed in that flowing fluid stream.

Once secondary flow circulation patterns are established, they will tend to persist in the stream. This "memory" with respect to secondary flow is used to advantage and allows for the disruption and consequent mixing when exiting from one curve or arc in the flow path and entering into a subsequent curve or arc, which is oriented to establish the secondary flow in a different path orientation. Thus, and assuming relatively stable laminar flow having a generally regular parabolic fluid stream component velocity graph in the generally straight coil inlet portion, changes in the respective velocities of different portions of the flowing fluid stream due to centrifugal forces and wall friction, as illustrated in FIG. 8, tend to distort the fluid stream component velocity graph from a generally regular paraboloid 22 to increasingly distorted paraboloids 24 and 26 as the fluid stream completes its transit of the initial coil 18. Such distortion results in the generation of stable secondary flow patterns oriented perpendicular to the flowing fluid stream, as illustrated generally at 30 and 32 in FIG. 9. As shown, these secondary flow patterns, will be generally symmetrical to a plane of symmetry or curvature as indicated at 40 and will contribute significantly to the mixing of the flowing fluid stream.

Certain portions of the flowing fluid stream, or what will hereinafter be termed "dead areas," as indicated generally at 42, 42', 44 and 44' in FIG. 9, lie without these secondary flow circulation patterns. Thus, and since all of the subsequent, coils of the representative prior art helical mixing coil here uner discussion are generally parallel to initial coil 18—see also, for example, FIG. 1 of U.S. Letters Pat. No. 2,933,293—the orientation of the secondary flow circulation patterns 30 and 32, and of the plane of symmetry or curvature 40, relative to the mixing coil conduit, will remain substantially unchanged during flow of the fluid stream throughout the entire mixing coil. Accordingly, fluid stream components which reside in the dead areas 42, 42' and 44 and 44' will remain generally unmixed. In addition, the substantially stable relative orientations of the secondary flow circulation patterns 30 and 32 will restrict the mixing effects due to repeated re-circulation along generally the same flow paths with little, if any, cross-mingling therebetween. More detailed illustration and description of the phenomenon of secondary flow attendant the flow of a fluid stream in a curved conduit is provided in *MEASUREMENT OF RADIAL TRANSPORT IN SLUG FLOW USING ENZYME TUBES,* by Horvath, C.; Solomon, B.; Engasser, J-M., Published by Industrial and Engineering Chemistry Fundamentals Vol. 12, No. 4, 1973, Pp. 431-439, and in *FLOW OF FLUIDS THROUGH VALVES, FITTINGS, AND PIPE,* Technical Paper No. 410, Published by Engineering Division of Crane Co., 300 Park Avenue, New York, N.Y. 10022, 1969, which are hereby incorporated by reference.

Returning now to FIGS. 1 and 2 for the detailed description of the mixing coil 12 of our invention, the same will be readily seen to comprise a plurality of interconnected arcuate sections having respective planes of curvature, which are non-parallel and, preferably, orthogonal. Such arcuate sections are indicated at 50, 52, 54, 56, 58, 60, 62, 64, 66, 68 and 70, respectively. It should be appreciated that a greater or lesser number of arcuate sections may be utilized, depending upon the particular mixing requirements. The tubing 72 which forms the mixing coil 12 may be made from any readily available, appropriately inert and durable material, for example, polytetrafluroethylene or glass.

The mixing coil 12 contains a relatively large number of abrupt turns or changes in direction per unit length to define an overall tortuous flow path. Thus, and considering only arcuate sections 58, 60 and 62 and assuming that coil 12 is generally horizontally oriented as illustrated in FIG. 1, the twin circulating patterns in the secondary flow of the fluid stream are forced to abruptly change orientation by 90° when passing from arcuate section 58 and through arcuate section 60, and to abruptly again change orientation by 90° when passing from arcuate section 60 and through arcuate section 62. The resulting sequence of circulation patterns is illustrated in FIGS. 3–7. Each abrupt reorientation of the secondary flow circulation patterns in the flowing fluid stream, or segment, completely destroys and reestablishes such secondary flow patterns therein. An efficient mixing results, due to the fact that turbulent mixing of the fluid stream, including dead areas, as therein indicated at 80, 80', 82 and 82', results during transition of the secondary flow circulation patterns to a new orientation, as illustrated in FIGS. 4 and 6.

Figure 3:
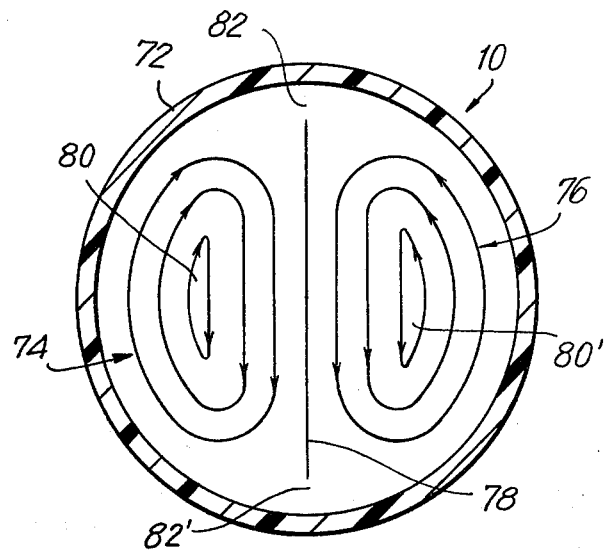
FIGS. 3, 4, 5, 6 and 7 are somewhat enlarged cross-sectional views taken generally along lines 3—3, 4—4, 5—5, 6—6 and 7—7, respectively, in FIG. 1.
Figure 4:
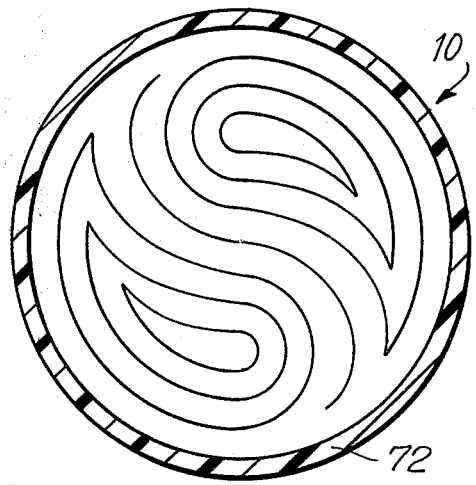
Figure 5:
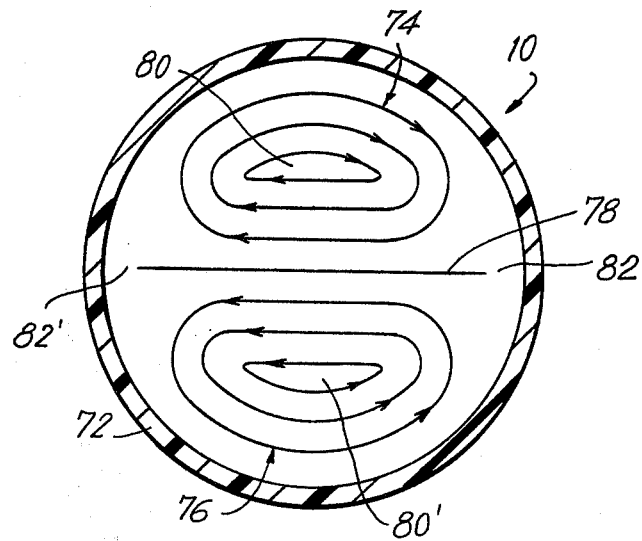
Figure 6:
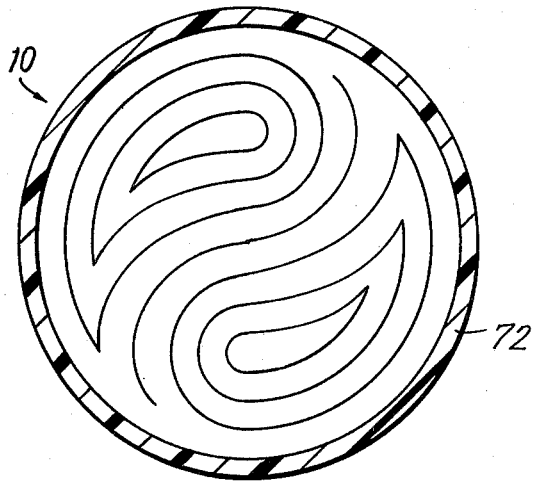

More specifically, and referring to the cross-sectional views of FIGS. 3, 4, 5, 6 and 7, respectively, the secondary flow circulation patterns and the planes of symmetry in the relevant portion of the flowing fluid stream generally at the locations in the mixing coil at which the cross-sectional views are taken, are illustrated. FIG. 3 illustrates the orientation of the fully developed stable secondary flow circulation patterns indicated generally at 74 and 76, and plane of symmetry, indicated at 78, relative to the tubing 72 of the mixing coil 12 of a portion of the fluid stream flowing generally downwardly in arcuate coil section 58. As this same portion of the fluid stream passes between generally downward flow in arcuate coil section 58 to generally horizontal flow in arcuate coil section 60, the secondary flow circulation patterns 74 and 76 become very significantly disturbed, as illustrated in FIG. 4, since the frictional forces and centrifugal forces act upon the flowing fluid stream in a markedly different direction. The application of such forces in a different direction completely disrupts and destroys the secondary flow circulation patterns 74 and 76, and continued flow along arcuate coil section 60 establishes new secondary flow circulation patterns 74 and 76 in a different orientation, as illustrated by FIG. 5. The relative orientations of the successive arcuate coil sections 58 and 60, and successive other arcuate sections should be such as to destroy and re-establish the secondary flow patterns in different orientations, as described. Preferably, a three-dimensional orthogonal relationship of the arcuate sections, as illustrated in FIG. 1, is utilized. However, and for a given flow rate, portions of each arcuate section can define an angle greater or less than 90° relative to the preceding arcuate section, so long as such angle is sufficient to establish a new orientation of the secondary flow circulation patterns in the fluid stream relative to the inner wall of conduit 72.

Figure 7:
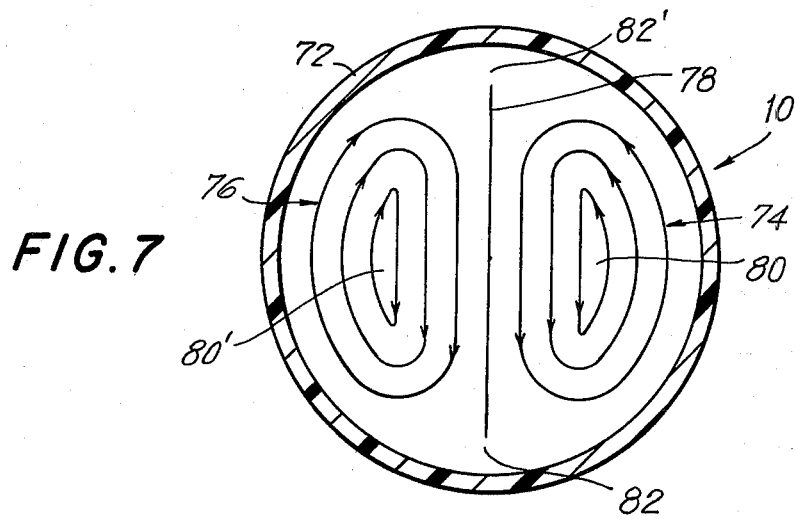

The subsequent complete destruction and re-establishment of the secondary flow circulation patterns 74 and 76, again reoriented by approximately 90° as occurs attendant passage of the fluid stream from arcuate section 60 into arcuate section 62, is illustrated in FIGS. 6 and 7.

The changes in direction of the flowing fluid stream from a generally doward flow in arcuate seftion 58 to a generally horizontal flow in arcuate section 60 to a generally upward flow in arcuate section 62 occur as described and depicted in the relatively short length of tubing which constitutes those arcuate sections. Between arcuate sections 58, 60 and 62, the secondary flow patterns will experience two complete, abrupt destructions and re-establishments, with attendant reorientations relative to tubing 72. For example, the entire length of mixing coil 12 may be less than 1½ inches from arcuate section 50 to arcuate section 70; it being clear that fully ten such complete and abrupt destructions and re-establishments of the secondary flow patters will advantageously occur in accordance with the teachings of our invention in that relatively short length.

Under the above circumstances, rapid and thorough mixing of two or more components in the fluid stream, whether of the same or different densities, will be effected by the flow through the mixing coil 12, configured according to the present invention. More specifically, and referring again to FIG. 3, the dead areas, as indicated at 80, 80, 82 and 82', in the fluid stream are continuously disrupted during passage of the fluid stream between the respective arcuate sections defined in mixing coil 12. In each instance, fluid contained in such dead areas is completely swept by the changing secondary flow patterns 74 and 76 to re-appear at markedly different locations relative to tubing 72 upon re-establishment of those stable, secondary flow patterns in the succeeding arcuate section. Thus, fluid stream components residing in these otherwise dead areas will, in each such instance, be extensively mixed with other rapidly moving portions of the stream. In addition, the repeated abrupt destructions and re-establishments, with attendant reorientations, of the secondary flow patterns 74 and 76, result in very thorough mixing of other fluid stream components caught up in those rapidly changing flow patterns. Thus, thorough mixing of all fluid stream components is assured. In fact, precisely controlled comparison tests conducted on the mixing coil of our invention and on representative prior art helical mixing coils having substantially the same winding diameter, have established the mixing coil of the present invention to be approximately four times as effective as the helical mixing coil per unit conduit length.

Figure 10:
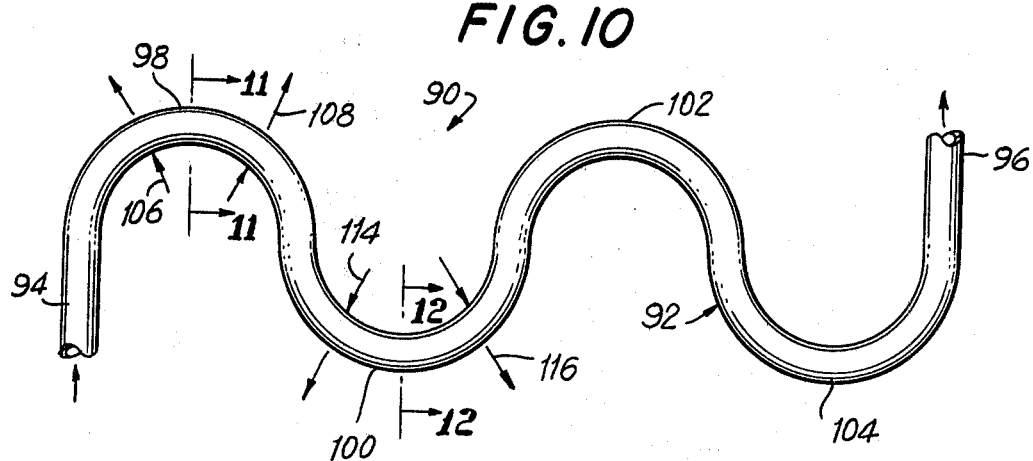
FIG. 10 is a side elevational view of another embodiment of new and improved mixing apparatus constructed and operative in accordance with the teachings of our invention.

Another embodiment of mixing apparatus constructed and operative in accordance with the teachings of our invention is indicated generally at 90 in FIG. 10 and, as seen therein, comprises a conduit 92 having a fluid stream inlet 94 and a fluid stream outlet 96; and including generally arcuate sections 98, 100, 102 and 104, respectively, which in essence reverse upon themselves as shown to result in the formation of a generally serpentine mixing coil, and one wherein the longitudinal axis of the conduit 92 remains generally in the same plane. With the mixing coil of our invention configured as depicted in FIG. 10, it may be readily understood that the fluid stream flowing therethrough will be subjected to generally oppositely directed centrifugal forces attendant the transit by the fluid stream of successive ones of the arcuate sections of the coil. For example, when flowing generally through arcuate section 98, the fluid stream will be subjected to generally upwardly directed centrifugal forces as indicated by the arrows 106 and 108 in FIG. 10 to result in the establishment of secondary flow patterns in the fluid stream as illustrated at 110 and 112 in FIG. 11. Subsequent flow of the fluid stream from arcuate section 98 into and through arcuate section 100 will result in a general reversal of the direction of these centrifugal forces to generally downwardly directed centrifugal forces as indicated by the arrows 114 and 116 in FIG. 10, with attendant complete destruction of the secondary flow patterns 110 and 112 of FIG. 11 and re-establishment thereof as illustrated at 118 and 120 in FIG. 12.

Figure 11:
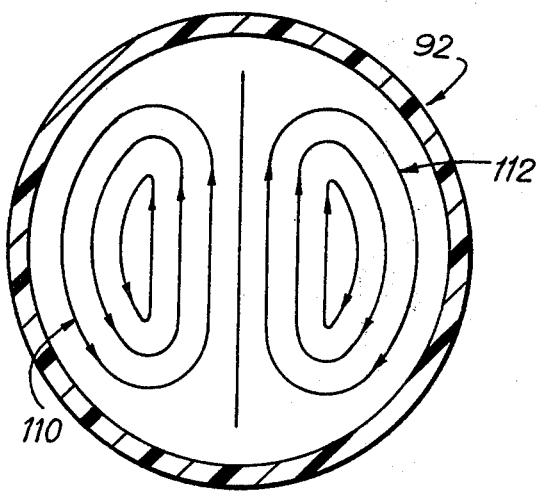
FIG. 11 is a cross-sectional view taken generaly along line 11—11 in FIG. 10.
Figure 12:
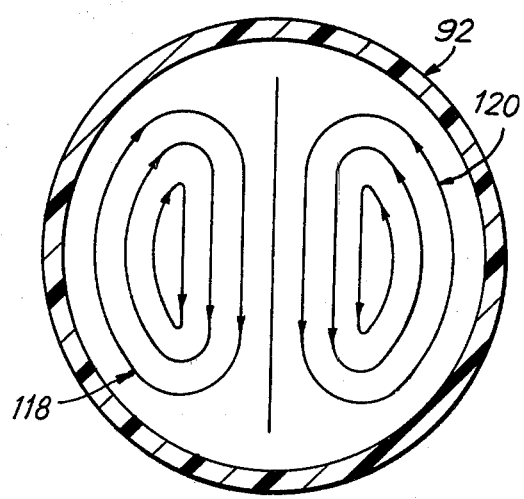
FIG. 12 is a cross-sectional view taken generally along line 12—12 in FIG. 10.

Careful comparison of the respective secondary flow patterns 110 and 112 of FIG. 11, and 118 and 120 of FIG. 12, makes clear that the orientations thereof relative to the conduit 92 have been completely reversed or shifted by approximately 180°. More specifically, it will readily be seen that the respective directions of rotation of those secondary flow patterns have been reversed or shifted from counterclockwise and clockwise for secondary flow patterns 110 and 112 in FIG. 11 to clockwise and counterclockwise for secondary flow patterns 118 and 120 in FIG. 12. Under these conditions, it will be clear that all relevant dead areas in the flowing fluid stream, as depicted and described in detail hereinabove with regard to FIGS. 3, 4, 5, 6 and 7, will be completely swept, again with particularly thorough co-mingling and mixing of the respective components of the flowing fluid stream. This same particularly thorough co-mingling and mixing of the respective fluid stream components will, of course, occur attendant the flow of the fluid stream from arcuate section 100 of the mixing apparatus 90 of FIG. 10 and through arcuate section 102, and attendant fluid stream flow from arcuate section 102 into and through arcuate section 104; it being here noted that a greater or lesser number of arcuate sections than those depicted and described herein may be included in mixing apparatus 90. A further embodiment of the mixing apparatus of our invention may take the general form of that depicted in FIG. 10, but wherein respective of the arcuate sections, or series thereof, as stacked in such manner that the longitudinal axes thereof lie in parallel or substantially parallel planes.

The new and improved mixing apparatus and method of our invention finds particular application in automated analytical continuous-flow systems, for example, as disclosed in U.S. Letters Pat. No. 3,479,141 issued Nov. 18, 1969 to William J. Smythe, et al, and assigned to the assignee hereof. In such systems, a segmented fluid stream comprises alternating liquid sample segments separated by segments of an appropriate immiscible fluid, e.g., silicone. Of course, any inert immiscible fluid, e.g., air, can be used for segmentation. Such fluid stream is reacted with appropriate reagents and requires thorough mixing with the same. The segmenting immiscible fluid prevents inter-segment contamination during flow along the system. The mixing action provided by the apparatus and method, as described hereinabove, effects such mixing without destroying the integrity and/or isolation of the successive segments.

Various changes may, of course, be made in the herein disclosed embodiment of our invention without departing from the spirit and scope of that invention as defined by the appended claims.

What is claimed is:

1. A method for the rapid and thorough, non-invasive mixing of two or more components in a fluid stream which is flowing in a single conduit comprising a single inlet and a single outlet which are connected by a single, undivided, unobstructed flow path that is closed to other flow paths, which method comprises the steps of:
   establishing a first secondary flow pattern in said fluid stream flowing in a first portion of said conduit; and, thereafter,
   establishing a second secondary flow pattern in said fluid stream flowing in a second portion of said conduit which is in close proximity to said first portion prior to the substantial dissipation of said first secondary flow pattern; and
   destroying said first secondary flow pattern in said fluid stream flowing in said second portion of said conduit which is in close proximity to said first portion by establishing said second secondary flow pattern therein.

2. The method of claim 1 wherein establishing said second secondary flow pattern comprises the step of establishing said second secondary flow pattern at a different orientation relative to the orientation of said first secondary flow pattern.

3. The method of claim 1 wherein the step of establishing said first secondary flow pattern comprises the step of flowing said fluid stream in a first arcuate section of said unobstructed conduit and establishing said second secondary flow pattern comprises the step of flowing said fluid stream in a second arcuate section of said conduit.

4. The method of claim 3 wherein the step of flowing said fluid stream in said first conduit section comprises the step of flowing said fluid stream in a first conduit section operable to establish said first secondary flow pattern in a first orientation, and the step of flowing said fluid stream in said second conduit section comprises the step of flowing said fluid stream in a conduit section operable to establish said second secondary flow pattern in a second and different orientation.

5. The method of claim 4 wherein said first and second orientations are generally opposite.

6. In apparatus for the rapid and thorough, non-invasive mixing of two or more components in a fluid stream which is flowing in a single conduit comprising a single inlet and a single outlet which are connected by a single, undivided, unobstructed flow path that is closed to other flow paths, the improvements comprising:
   means along a first portion of said conduit to establish a first secondary flow pattern in said fluid stream flowing in said conduit; and
   means along a second portion of said conduit positioned in close proximity and relative to said first means so as to establish a second secondary flow pattern in said fluid stream flowing in said conduit prior to the substantial dissipation of said first secondary flow pattern which is effective to destroy said first secondary flow pattern.

7. The apparatus of claim 6 wherein said means to establish said second secondary flow pattern is operable to establish said second secondary flow pattern at a different orientation relative to said first secondary flow pattern.

8. The apparatus of claim 6 wherein said means to establish said first secondary flow pattern comprises a first section of said unobstructed conduit, said means to establish said second secondary flow pattern comprises a second section of said unobstructed conduit, and said means to destroy said first secondary flow pattern comprises means for connecting said first and second conduit sections.

9. The apparatus of claim 8 wherein said first and second conduit sections are generally arcuate.

10. The apparatus of claim 8 wherein said first section of said unobstructed conduit is operable to establish a secondary flow pattern of a first orientation, and said second section of unobstructed conduit is operable to establish a secondary flow pattern of a second and different orientation.

11. The apparatus of claim 8 wherein said first and second conduit sections are generally mutually orthogonal.

12. Apparatus for the rapid and thorough, non-invasive mixing of two or more components of a fluid stream, which apparatus comprises a single conduit having a single inlet and a single outlet which are connected by a single, undivided, unobstructed flow path that is closed to other flow paths and defining a plurality of bends, successive ones of said bends having respective planes of curvature which are relatively oriented to impart successive changes in the direction of flow of a fluid stream passed therealong, each of said bends being positioned in close proximity and relative to the previous bend to establish a new secondary flow pattern in said fluid stream, prior to the substantial dissipation of the previous secondary flow pattern, said new secondary flow pattern being directed by the plane of curvature of the bend by which it is established and in an orientation which makes it effective to destroy said first secondary flow pattern.

13. The apparatus of claim 12, wherein said plurality of bends are formed in a tortuous fashion, such that at least selected ones of said bends have non-parallel planes of curvature.

14. The apparatus of claim 13, wherein said plurality of bends are formed in tortuous fashion, such that successive ones of said bends have substantially orthogonal planes of curvature.

15. The apparatus of claim 12, wherein said plurality of bends are formed in serpentine fashion, such that at least selected ones of said bends have planes of curvature located in a same plane.

16. The apparatus of claim 12, wherein said plurality of bends are formed in serpentine fashion, such that at least selected ones of said bends have planes of curvature located in substantially parallel planes.

17. The apparatus of claim 12, wherein selected ones of said bends define arcuate sections.

18. The apparatus of claim 12, wherein selected ones of said bends are formed at right angles.

* * * * *